United States Patent
Yoshikawa et al.

(10) Patent No.: US 8,071,832 B2
(45) Date of Patent: Dec. 6, 2011

(54) **METHOD OF CONVERTING ETHYLBENZENE AND PROCESS FOR PRODUCING *P*-XYLENE**

(75) Inventors: Takahiro Yoshikawa, Nagoya (JP); Masatoshi Watanabe, Nagoya (JP); Ryoji Ichioka, Nagoya (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 12/933,118

(22) PCT Filed: Mar. 18, 2009

(86) PCT No.: PCT/JP2009/055258
§ 371 (c)(1),
(2), (4) Date: Sep. 17, 2010

(87) PCT Pub. No.: WO2009/116561
PCT Pub. Date: Sep. 24, 2009

(65) Prior Publication Data
US 2011/0021854 A1 Jan. 27, 2011

(30) Foreign Application Priority Data

Mar. 19, 2008 (JP) .................. 2008-071592

(51) Int. Cl.
*C07C 4/18* (2006.01)
(52) U.S. Cl. ........................ 585/489; 585/488
(58) Field of Classification Search .................. 585/488, 585/489
See application file for complete search history.

(56) References Cited

U.S. PATENT DOCUMENTS

| 4,695,667 A | 9/1987 | Sumitani et al. |
| 4,899,001 A | 2/1990 | Kalnes et al. |
| 2005/0010074 A1* | 1/2005 | Iwayama et al. .............. 585/481 |

FOREIGN PATENT DOCUMENTS

| EP | 2 008 988 A1 | 12/2008 |
| EP | 2 027 917 A1 | 2/2009 |
| JP | 49-46606 | 12/1974 |
| JP | 57-200319 | 12/1982 |
| JP | 5-24661 | 2/1993 |
| JP | 5-87054 | 12/1993 |
| JP | 8-16074 | 2/1996 |
| WO | 2005/071045 A1 | 8/2005 |
| WO | WO 2007/114127 A1 | 10/2007 |

* cited by examiner

*Primary Examiner* — Thuan Dinh Dang
(74) *Attorney, Agent, or Firm* — DLA Piper LLP (US)

(57) ABSTRACT

A process converts ethylbenzene in a C8 aromatic hydrocarbon mixture containing a large amount of non-aromatic hydrocarbons, mainly to benzene, by which the xylene loss is small, the deactivation rate of the catalyst can be reduced, and a high conversion rate to p-xylene can be attained. The process for converting ethylbenzene includes bringing a feedstock containing an alicyclic hydrocarbon(s) in an amount of not less than 1.0% by weight, ethylbenzene and xylene into contact with hydrogen in the presence of a catalyst to convert ethylbenzene mainly to benzene, wherein the catalyst is mainly composed of MFI zeolite and an inorganic oxide(s) and rhenium-supported, and wherein the conversion is carried out at a reaction pressure of not less than 1.0 MPa-G.

12 Claims, 5 Drawing Sheets

METHOD OF CONVERTING ETHYLBENZENE AND PROCESS FOR PRODUCING P-XYLENE

RELATED APPLICATIONS

This is a §371 of International Application No. PCT/JP2009/055258, with an international filing date of Mar. 18, 2009, which is based on Japanese Patent Application No. 2008-071592, filed Mar. 19, 2008, the subject matter of which is incorporated by reference.

TECHNICAL FIELD

This disclosure relates to a process for converting ethylbenzene and process for producing p-xylene. More particularly, the disclosure relates to a process for converting ethylbenzene to mainly benzene, which ethylbenzene is contained in a feedstock containing an alicyclic hydrocarbon(s) in an amount of not less than 1.0% by weight, ethylbenzene and xylene, by which the xylene loss is small, the deactivation rate of the catalyst can be reduced, and a high conversion rate to p-xylene can be attained, as well as to a process comprising purifying C8 aromatic hydrocarbon mixture from the product obtained by the above-described conversion, and then separating p-xylene.

BACKGROUND

Among xylene isomers, the most industrially important one is p-xylene. At present, p-xylene is used as a raw material for producing terephthalic acid, which is a monomer constituting polyesters that are ranked with nylons as major polymers. Its demand is high especially in Asia in recent years, and this trend is expected not to change in the future. On the other hand, since the demands of other xylene isomers, o-xylene and m-xylene, are much smaller than that of p-xylene, it is industrially important to convert o-xylene and m-xylene to p-xylene.

The raw material of p-xylene is a C8 aromatic hydrocarbon mixture. Since C8 aromatic hydrocarbon mixture generally contains high boiling components having not less than 9 carbon atoms in addition to xylene isomers and ethylbenzene, these high boiling components are first removed by distillation. The purified C8 aromatic hydrocarbon mixture is supplied to p-xylene-separating step to separate p-xylene. Since the boiling points of xylene isomers and ethylbenzene are close, it is difficult to separate p-xylene by distillation. Therefore crystallization or adsorptive separation is utilized.

In the case of crystallization, since a eutectic mixture of p-xylene, other xylene isomers and ethylbenzene is generated, the recovery of p-xylene per one path is limited, and is usually limited to about 60% at most. In case of crystallization, the higher the concentration of the p-xylene in the C8 aromatic hydrocarbon mixture supplied to the crystallization, not only the higher the productivity, but also the higher the recovery of p-xylene per one path.

In the case of adsorptive separation, almost 100% of p-xylene can be recovered in one path. In the adsorptive separation, the key component in the C8 aromatic hydrocarbons, which most strongly inhibits the separation of p-xylene, is ethylbenzene. Therefore, by decreasing the concentration of ethylbenzene in the C8 aromatic hydrocarbon mixture supplied to the adsorptive separation, since the load of the adsorptive separation can be decreased due to the decrease in ethylbenzene which is an obstacle to the separation, and since the p-xylene concentration in the C8 aromatic hydrocarbon mixture to be supplied to the adsorptive separation can be increased, the production capacity of p-xylene in the same adsorptive separation equipment can be increased.

The C8 aromatic hydrocarbons from the p-xylene-separation step, having a low concentration of p-xylene, are then transferred to a xylene-isomerization step and xylene isomers are isomerized with a zeolite catalyst to a p-xylene concentration close to that in the thermodynamic equilibrium composition. After removing the by-products having lower boiling points than the C8 aromatic hydrocarbons by distillation, the resulting product is mixed with the above-described fresh C8 aromatic hydrocarbon mixture and the resulting mixture is recycled to high boiling components separation step to remove by distillation the high boiling components having not less than 9 carbons, followed by separation and recovery of p-xylene again in the p-xylene separation step. This series of cycle is hereinafter referred to as "separation-isomerization cycle".

FIG. 4 is a flow chart showing this "separation-isomerization cycle". Usually, the C8 aromatic hydrocarbon mixture which is the raw material of p-xylene is transferred to a high boiling components separation step 1 from the supply line denoted by stream 36. In cases where it is desired to remove the low boiling components contained in the fresh C8 aromatic hydrocarbon mixture, the mixture is supplied to a low boiling components separation step 4 from the supply line denoted by stream 45. In some cases where it is not necessary to remove the high boiling components and the low boiling components, the fresh C8 aromatic hydrocarbon mixture is directly supplied to a p-xylene-separation step 2 from the supply line denoted by stream 46. In either case, the fresh C8 aromatic hydrocarbon mixture is transferred to the p-xylene-separation step 2 together with C8 aromatic hydrocarbon components isomerized to attain a p-xylene concentration close to that in the thermodynamic equilibrium composition in a xylene-isomerizing step 3. In the high boiling components separation step 1, the high boiling components are removed through a line denoted by stream 38. The C8 aromatic hydrocarbons from which the high boiling components have been removed are transferred to the p-xylene-separation step 2 through a line denoted by stream 37, and p-xylene is separated through the line denoted by stream 39. The C8 aromatic hydrocarbons having a low p-xylene concentration are transferred to the xylene-isomerizing step 3 through a line denoted by stream 40, and isomerized to attain a p-xylene concentration close to that in the thermodynamic equilibrium composition. To the xylene-isomerizing step, hydrogen or a hydrogen-containing gas is also transferred through a line denoted by stream 41. The C8 aromatic hydrocarbon mixture from the xylene-isomerizing step, which contains by-products, is transferred to a low boiling components separation step 4 through a line denoted by stream 42, and the low boiling components such as benzene and toluene generated as by-products in the xylene-isomerizing step are removed through the line denoted by stream 43. The p-xylene-enriched stream containing high boiling components is transferred to the high boiling components separation step 1 through the line denoted by stream 44. The p-xylene-enriched stream is again recycled to the p-xylene-separation step 2 after removing in the high boiling components separation step 1 the high boiling components generated as by-products in the xylene-isomerizing step.

As described above, the C8 aromatic hydrocarbon mixture supplied to the "separation-isomerization cycle" contain ethylbenzene. In the above-described "separation-isomerization cycle", the ethylbenzene is not removed and remains in the cycle, so that ethylbenzene accumulates. If the ethylbenzene is removed in some way to prevent accumulation thereof, ethylbenzene in an amount corresponding to the degree of removal thereof circulates in the "separation-isomerization cycle". If the amount of the circulating ethylbenzene is decreased, the total amount of the circulation is also decreased, so that the energy unit consumption is decreased, which is greatly advantageous from the economical viewpoint. In addition, since the p-xylene concentration is increased and the ethylbenzene concentration is decreased in the C8 aromatic hydrocarbon mixture to be supplied to the p-xylene-separation step, the load in the p-xylene-separation step can also be decreased, which leads to the increase in the production of p-xylene.

The methods for removing ethylbenzene usually employed include the method in which an ability to convert ethylbenzene is given to the isomerization catalyst used in the xylene-isomerizing step, thereby converting ethylbenzene to xylene or to a substance which can be easily separated from xylene, in the isomerization step, that is, the reforming method in which ethylbenzene is isomerized to xylene simultaneously with the isomerization of xylene in the isomerization step (for example, JP 49-46606 B); and the dealkylation method in which ethylbenzene is converted to benzene and ethane by hydrogenation and dealkylation thereof in the isomerization step of xylene, and then the benzene is separated by distillation in the subsequent distillation step (for example, JP 57-200319 A).

In the reforming method, since it is necessary to give to the catalyst hydrogenation/dehydrogenation ability, it is indispensable that the catalyst contain platinum which is a very expensive noble metal. Further, to convert ethylbenzene to xylene, the reaction mechanism requires mediating the reaction through a non-aromatic hydrocarbon such as naphthene or paraffin, and the non-aromatic hydrocarbon exists in the product at a concentration from several percent to ten and several percent, and circulates in the "separation-isomerization cycle". Further, since the ethylbenzene conversion rate in the reforming method is restricted by the thermodynamic equilibrium, the conversion rate is only about 20% to 50%.

On the other hand, in the dealkylation method, since only the hydrogenation ability to hydrogenate the ethylene generated by dealkylation of ethylbenzene is need to be given to the catalyst, a hydrogenation-active metal which is less expensive than platinum may be used, or even when platinum is used, the content thereof can be largely reduced, so that the catalyst is inexpensive. Further, since the reaction between ethylene and hydrogen is very quick, which ethylene is generated by the dealkylation reaction of ethylbenzene, the dealkylation reaction of ethylbenzene proceeds as if it is a substantially non-equilibrium reaction, and a very high ethylbenzene conversion rate can be attained.

Under these circumstances, the dealkylation method in which the catalyst is inexpensive and the amount of circulating substances in the "separation-isomerization cycle" can be made smaller is mainly used.

In converting the ethylbenzene in ethylbenzene-containing C8 aromatic hydrocarbons to benzene by dealkylation and in isomerizing o-xylene and m-xylene to p-xylene, (1) to make the ethylbenzene conversion rate as high as possible is preferred to decrease the energy unit consumption for the production of p-xylene so as to increase the production of p-xylene; (2) to make the conversion rate to p-xylene as high as possible is preferred to increase the p-xylene concentration in the C8 aromatic hydrocarbons circulating in the "separation-isomerization cycle" so as to promote the productivity of p-xylene; and (3) to make the xylene loss as small as possible is preferred to decrease the raw material unit consumption in the p-xylene production so as to decrease the production cost of p-xylene.

On the other hand, the usually used raw material of p-xylene is the C8 aromatic hydrocarbon mixture which is the reformate obtained by reforming naphtha and subsequent fractional distillation. A representative composition of this C8 aromatic hydrocarbon mixture is as follows: ethylbenzene: 18% by weight, p-xylene: 19% by weight, m-xylene: 42% by weight, and o-xylene: 21% by weight. However, with the increase in the demand of p-xylene, supply of the above-described reformate C8 aromatic hydrocarbon mixture tends to be short. Further, under the circumstances where it is emphasized that the amount of petroleum resources in the world is limited and petroleum will deplete in some day, C8 aromatic hydrocarbon mixture generated from thermal cracking, hereinafter referred to as "pyrolysis gasoline", is now attracting attention. A representative composition of such "pyrolysis gasoline" is as follows: ethylbenzene: 60% by weight, p-xylene: 8% by weight, m-xylene: 19% by weight, and o-xylene: 10% by weight, non-aromatic components: 3% by weight.

When compared with the reformate C8 aromatic hydrocarbon mixture, since "pyrolysis gasoline" has a higher ethylbenzene concentration, ethylbenzene accumulates in the "separation-isomerization cycle" and the amount of the ethylbenzene circulating in the "separation-isomerization cycle" is increased, so that the load in the p-xylene-separation step is increased, which leads to decrease in the p-xylene production, only a limited amount thereof has been used so far. Further, "pyrolysis gasoline" much contains not only ethylbenzene, but also non-aromatic hydrocarbons. Thus, when the dealkylation method is used, because of the large amount of the non-aromatic hydrocarbons circulating in the "separation-isomerization cycle", the xylene loss in the xylene-isomerizing step is sharply increased and the deactivation rate of the catalyst is increased, which are problematic.

In view of these circumstances, in the conversion of ethylbenzene to benzene and ethane by the dealkylation method, the following four points are industrially important tasks for attaining increase in the production of p-xylene, decrease in the raw material unit consumption and energy unit consumption, and attaining stable supply of the raw material:

(1) A high ethylbenzene conversion rate can be attained.

(2) The feedstock containing non-aromatic hydrocarbons can be treated without increasing the deactivation rate of the catalyst.

(3) Xylene loss can be made small even if the ethylbenzene conversion rate is made high.

(4) A high conversion rate to p-xylene can be attained.

As a method by which xylene loss is small even if the ethylbenzene conversion rate is made high in the conversion of ethylbenzene to benzene and ethane by the dealkylation reaction, a method wherein a zeolite having a crystal size larger than 1 μm is used to decrease the diffusion rate of o-xylene (e.g., JP 8-16074 B) has been tried.

However, even if such a method is used, with a raw material such as "pyrolysis gasoline", having a high ethylbenzene concentration and containing non-aromatic hydrocarbons in a large amount, the xylene loss is sharply increased.

In the isomerization reaction of xylene, if the reaction pressure is increased, bimolecular reaction such as the disproportionation reaction and transalkylation reaction, and aromatics ring hydrogenation, preferentially occur, so that xylene loss and generation of non-aromatic hydrocarbons are increased. Further, if a catalyst containing platinum is used as the hydrogenation/dehydrogenation component, the price of the catalyst is high. In addition, since the hydrogenation reaction of the aromatic hydrocarbons drastically proceeds due to the raise of the reaction pressure and reaction temperature, not only the xylene loss is increased, but also the recovery of the aromatic hydrocarbons is decreased (e.g., U.S. Pat. No. 4,899,001 B (Table 1)), which are problematic.

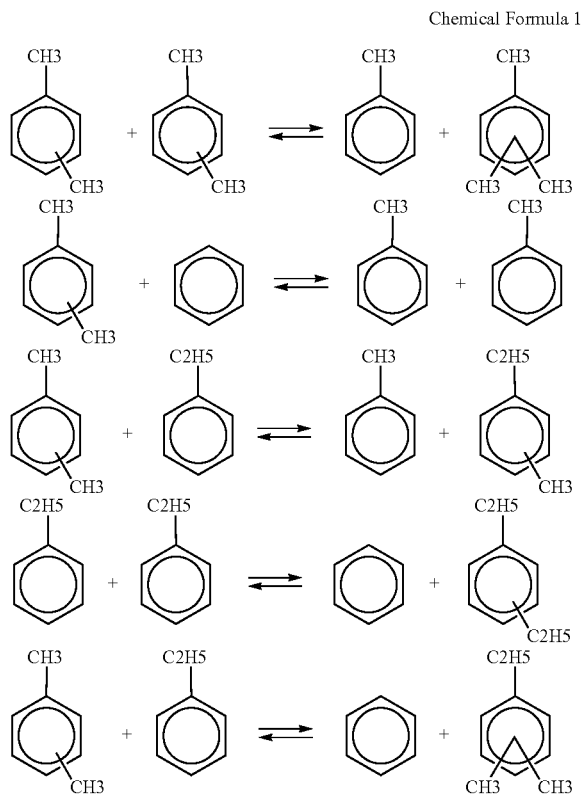

Chemical Formula 1

The methods for further decreasing the amount of the circulating ethylbenzene in the "separation-isomerization cycle" include a method wherein the ethylbenzene in the C8 aromatic hydrocarbon mixture is treated by the above-described dealkylation method to convert the ethylbenzene mainly to benzene and the generated benzene is separated by distillation before feeding the C8 aromatic hydrocarbon mixture to the "separation-isomerization cycle", thereby largely decreasing the circulation of the ethylbenzene in the "separation-isomerization cycle" (e.g., JP 5-87054 B); and a method wherein the C8 aromatic hydrocarbon mixture is supplied to a xylene-isomerizing step having an ability of hydrogenation and dealkylation, and then the product is supplied to a p-xylene-separating step (e.g., JP 5-24661 A).

These methods are similar to the isomerization reaction in the "separation-isomerization cycle" in the respect that the reaction to convert ethylbenzene to benzene and ethane by dealkylation reaction is carried out. However, in cases where the former method is used, since the feedstock is not diluted with the C8 aromatic hydrocarbons circulating in the "separation-isomerization cycle", especially in cases where "pyrolysis gasoline" containing large amount of non-aromatic hydrocarbons is used as the feedstock, the xylene loss is extremely increased and the deactivation rate of the catalyst is drastically increased. In cases where the latter method is used, although the feedstock is diluted with the C8 aromatic hydrocarbons circulating in the "separation-isomerization cycle", since the amount of the feedstock of xylene-isomerization step is increased, even if the xylene loss is slightly increased, its influence on the raw material unit consumption is large, which is problematic. Thus, in cases where "pyrolysis gasoline" containing a large amount of non-aromatic hydrocarbons is used, if the prior art technique is applied, the deactivation rate of the catalyst is sharply increased and the xylene loss is also increased, so that the catalyst life is shortened and the raw material unit consumption is largely aggravated, which are problematic. Therefore, when "pyrolysis gasoline" containing a large amount of ethylbenzene is used and so the amount of the ethylbenzene circulating in the "separation-isomerization cycle" is desired to be decreased, these processes cannot be employed.

It could therefore be helpful to provide a process for converting ethylbenzene in a C8 aromatic hydrocarbon mixture containing a large amount of non-aromatic hydrocarbons to mainly benzene, by which xylene loss is small, the deactivation rate of the catalyst can be reduced, and a high conversion rate to p-xylene can be attained.

It could also be helpful to provide a process for producing p-xylene, by which the concentration of ethylbenzene in the C8 aromatics hydrocarbon mixture for p-xylene-separation step can be largely decreased.

SUMMARY

We discovered that, among the non-aromatic hydrocarbons, especially alicyclic hydrocarbons increase the xylene loss, increase the deactivation rate of the catalyst, and decrease the conversion rate to p-xylene.

We also discovered that when a feedstock of xylene-isomerization step containing a large amount of alicyclic hydrocarbons contacts with a catalyst containing rhenium, surprisingly, by increasing the reaction pressure, by-production of non-aromatic hydrocarbons, the disproportionation reaction, and the transalkylation reaction can be reduced, and the xylene loss due to the non-aromatic hydrocarbons circulating in the "separation-isomerization cycle", and due to the by-production of toluene and C9+aromatic hydrocarbons can be decreased, thereby reaching the present invention. Further, we discovered that the deactivation rate of the catalyst can be largely reduced by increasing the amount of hydrogen supplied to the feedstock.

We thus provide:

(1) A process for converting ethylbenzene, the process comprising bringing a feedstock containing an alicyclic hydrocarbon(s) in an amount of not less than 1.0% by weight, ethylbenzene and xylene into contact with hydrogen in the presence of a catalyst to convert ethylbenzene mainly to benzene, wherein the catalyst is mainly composed of MFI type zeolite and an inorganic oxide(s) and supports rhenium, and wherein the conversion is carried out at a reaction pressure of not less than 1.0 MPa-G.

(2) A process for producing p-xylene, the process comprising the steps of:

subjecting a feedstock containing an alicyclic hydrocarbon(s) in an amount of not less than 1.0% by weight, ethylbenzene and xylene to the process according to the above-described process of the present invention, thereby converting the ethylbenzene in the feedstock to mainly benzene;

purifying C8 aromatics hydrocarbon mixture, preferably one comprising mainly xylene, or purifying xylene from the obtained reaction product by distillation; and thereafter, feeding the purified C8 aromatics hydrocarbon mixture, preferably one comprising mainly xylene, or purified xylene to a p-xylene separation step.

In converting the ethylbenzene in the C8 aromatic hydrocarbon mixture containing a large amount of alicyclic hydrocarbons to mainly benzene, the deactivation rate of the catalyst can be reduced and a high conversion rate to p-xylene can be attained. Further, by converting the C8 aromatic hydrocarbon mixture containing a large amount of alicyclic hydrocarbons to mainly benzene, and by decreasing the load on the p-xylene-separation step and decreasing the amount of the ethylbenzene circulating in the "separation-isomerization cycle", increase in the production of p-xylene and improvements in the energy unit consumption and raw material unit consumption can be attained.

Figure 1:
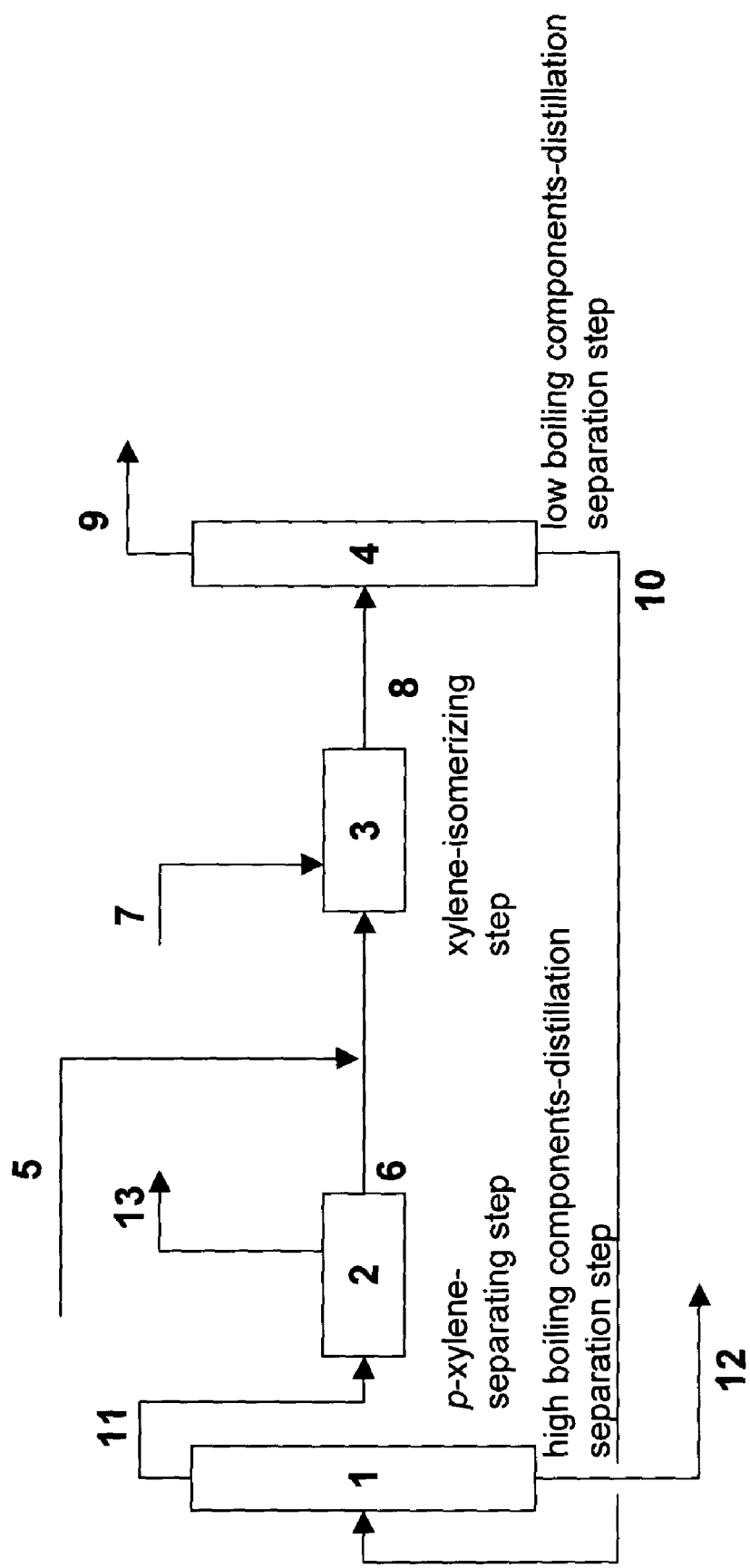
FIG. 1 is a conceptual diagram showing the flow of the "separation-isomerization cycle" for the improved production of p-xylene, to which the process may preferably be applied.

DESCRIPTION OF THE REFERENCE NUMERALS 1 high boiling components separation step
2 p-xylene-separating step
3 xylene-isomerizing step
4 low boiling components separation step
5 stream
6 stream
7 stream
8 stream
9 stream
10 stream
11 stream
12 stream
13 stream
14 stream
15 stream
16 stream
17 stream
18 stream
19 stream
20 stream
21 stream
22 stream
24 dealkylation step of ethylbenzene
25 stream
26 stream
27 stream
28 stream
29 stream
30 stream
31 stream
32 stream
33 stream
34 stream
35 stream
36 stream
37 stream
38 stream
39 stream
40 stream
41 stream
42 stream
43 stream
44 stream
45 stream
46 stream

DETAILED DESCRIPTION

The process is applied to a reaction by which the ethylbenzene in a feedstock is converted mainly to benzene. The term "converted mainly to benzene" means that the ratio (hereinafter referred to as "benzene selectivity") of the amount of generated benzene to the amount of the converted ethylbenzene is not less than 80 mol %. Examples of the conversion reaction to a substance other than benzene include the reaction wherein benzene and diethylbenzene are generated by the disproportionation of ethylbenzene; the reaction wherein ethylmethylbenzene and toluene are generated by the transalkylation of ethylbenzene and xylene; and the reaction wherein non-aromatic hydrocarbons are generated by the aromatic ring hydrogenation of ethylbenzene. Since a bimolecular reaction preferentially occurs in the reactions wherein the ethylbenzene is mainly subjected to disproportionation or transalkylation, a catalyst containing zeolite such as mordenite having a 12-membered oxygen ring having a relatively large pore size is used, and so the effect is small. On the other hand, in the reaction wherein non-aromatic hydrocarbons are generated by the aromatic ring hydrogenation of ethylbenzene, that is, in the above-described reforming method or the like, since platinum having hydrogenation/dehydrogenation ability is contained in the catalyst and so the alicyclic components contained in the feedstock can be converted to aromatic components, increase in the xylene loss, increase in the deactivation rate of the catalyst and the like have not been observed.

By applying our methods to a feedstock containing an alicyclic hydrocarbon(s) in an amount of not less than 1.0% by weight, the effects of decreasing xylene loss, increase in the conversion rate to p-xylene and inhibiting deactivation of the catalyst are obtained. The higher the content of the alicyclic hydrocarbon(s) in the feedstock, the larger these effects. On the other hand, a part of the alicyclic hydrocarbon(s) contained in the feedstock remains in the reaction product, and similar to ethylbenzene, the amount thereof corresponding to the degree of removal thereof circulates in the "separation-isomerization cycle", so that there is an upper limit of the preferred content of the alicyclic hydrocarbon(s) in the feedstock from the economical viewpoint. The improvement is obtained when the content of the alicyclic hydrocarbon(s) in the feedstock is preferably 1.0% by weight to 16% by weight, more preferably 3.0% by weight to 16% by weight, most preferably 10% by weight to 16% by weight. The feedstock may contain a single kind of alicyclic hydrocarbon or may contain a plurality of kinds of alicyclic hydrocarbons.

The alicyclic hydrocarbons are cycloalkanes which are saturated hydrocarbons; cycloalkenes which are unsaturated hydrocarbons and contain a double bond in the ring; and so on, and the effects are obtained for any of these alicyclic hydrocarbons. Especially, the effects are large when a cycloalkane(s) exist(s). The cycloalkane(s) include monocycloalkanes which are monocyclic saturated hydrocarbons, bicycloalkanes which are bicyclic saturated hydrocarbons and so on, and the effects are obtained for any of these cycloalkanes. The effects of the present invention are the largest in cases where monocycloalkane(s) exist(s). Among the monocycloalkanes, the effects are prominent when the present invention is applied to a feedstock containing alkylmonocycloalkane(s). Examples of the alicyclic hydrocarbons include monocycloalkanes such as cyclopentane, cyclohexane, methylcyclopentane, methylcyclohexane, dimethylcyclopentane, ethylcyclopentane, dimethylcyclohexane, ethylcyclohexane, propylcyclopentane, ethylmethylcyclopentane, trimethylcyclohexane, propylcyclohexane, ethylmethylcyclohexane, diethylcyclopentane, methylpropylcyclopentane and the like; bicycloalkanes such as bicyclo[2.1.1]hexane, bicyclo[2.2.0]hexane, bicyclo[3.1.0]hexane, bicyclo[2.2.1]heptane, bicyclo[3.1.1]heptane, bicyclo[3.2.0]heptane, bicyclo[4.1.0]heptane, bicyclo[2.2.2]octane, bicyclo[3.2.1]octane, bicyclo[3.3.0]octane, bicyclo[4.1.1]octane, bicyclo[4.2.0]octane, bicyclo[5.1.0]octane; cycloalkenes such as cyclopentene, cyclohexene, methylcyclopentene, methylcyclohexene, dimethylcyclopentene, ethylcyclopentene, dimethylcyclohexene, ethylcyclohexene, propylcyclopentene, ethylmethylcyclopentene, trimethylcyclohexene, propylcyclohexene, ethylmethylcyclohexene, diethylcyclopentene, methylpropylcyclopentene; and the like. The effects are large when the above-described monocycloalkane(s) and/or bicycloalkane(s) exist(s), and monocycloalkane(s) is (are) more preferred. In cases where the alicyclic hydrocarbon(s) is (are) alkyl monocycloalkane(s) such as methylcyclopentane, methylcyclohexane, dimethylcyclopentane, ethylcyclopentane, dimethylcyclohexane, ethylcyclohexane, propylcyclopentane, ethylmethylcyclopentane, trimethylcyclohexane, propylcyclohexane, ethylmethylcyclohexane, diethylcyclopentane, methylpropylcyclopentane and the like, the most prominent effect may be obtained.

The reasons why the feedstock containing an alicyclic hydrocarbon specifically accelerates the deactivation rate of the catalyst, decreases the conversion rate to p-xylene and increases the xylene loss is presumably as follows:

1) Increase in Deactivation Rate of the Catalyst

When alicyclic hydrocarbons are decomposed on a site of solid acid of zeolite, olefin components and paraffin components are generated. Since the number of hydrogen atoms per a carbon atom in alicyclic hydrocarbons is smaller than paraffin components, a larger amount of olefin components are generated in decomposition thereof than in decomposition of paraffin components. It is thought that unless the olefin components are immediately hydrogenated to be converted to paraffin components, polymerization reaction thereof occurs on the solid acid sites of zeolite and the polymer coats the solid acid sites, thereby increasing the deactivation rate of the catalyst.

Platinum component which is a typical component as a hydrogenation-active component has extremely high hydrogenation activities to both aromatics ring and olefin components. Therefore, the platinum-supported catalysts have a characteristic in that when the partial pressure of hydrogen is increased by increasing the reaction pressure, the aromatics ring hydrogenation preferentially proceeds so that the loss of aromatic components are drastically increased. On the other hand, rhenium component has a characteristic in that the aromatics ring hydrogenation activity is low, and the hydrogenation activity to olefin components is high although not as high as that of platinum component.

Therefore, it is thought that the deactivation rate of the catalyst caused by the existence of the alicyclic hydrocarbons is smaller with platinum component than with rhenium component. However, rhenium component has a characteristic in that the loss of aromatic components is extremely small because the aromatics ring hydrogenation activity is extremely low.

2) Decrease in Conversion Rate to p-xylene

It is thought that olefin components are polymerized on the solid acid sites to poison the solid acid sites, so that the isomerization reaction of xylene which occurs at the same solid acid sites is inhibited.

3) Increase in Xylene Loss

When the solid acid sites are coated due to the polymerization of olefins and so the number of effective solid acid sites is decreased, the catalyst activity is decreased. Therefore, it is necessary to raise the reaction temperature. However, since the activation energy of the transalkylation reaction between the generated benzene and xylene, or the activation energy of the disproportionation reaction between xylene molecules is higher than the activation energy of the isomerization reaction of xylene, the transalkylation reaction or the disproportionation reaction is more likely to occur than the isomerization reaction when the reaction temperature is high, so that increase in the xylene loss is caused.

Especially, in MFI zeolite, the pores are formed with 10-membered oxygen rings. The pore size is smaller than that in mordenite in which the pores are formed with 12-membered oxygen rings, and is closer to the minimum molecular diameter of aromatic hydrocarbon components such as xylene. It is thought that with the deposition of olefin polymer in the vicinity of the pores, the pore size of the MFI zeolite becomes smaller and smaller, and benzene, toluene and xylene (especially p-xylene) which are likely to enter the pores are subjected to transalkylation reaction in the pores, so that the toluene having a small molecular diameter is likely to be generated.

Because of the above reasons, when the rhenium-supported catalyst which mainly composed of MFI zeolite and an inorganic oxide(s) is used, especially increase of the reaction pressure improves the hydrogenation activity of rhenium, as the result, the effect to reduce xylene loss by inhibiting the coating of the solid acid sites due to the polymerization of olefins by quickly converting the large amount of olefin components to paraffin components, which olefin components are generated by the decomposition of alicyclic hydrocarbons, is larger than the effect to accelerate the transalkylation reaction by increasing the reaction pressure.

The feedstock contains ethylbenzene. Although the content of ethylbenzene is not restricted, to keep the ethylbenzene concentration after the reaction low, a larger content of ethylbenzene in the feedstock requires a higher ethylbenzene conversion rate, so that the reaction temperature is high, the load to the catalyst increases and the xylene loss also increases. That is, the higher the content of ethylbenzene in the feedstock, the higher the effect to reduce the xylene loss by the process of converting ethylbenzene. The method is effective for the feedstock containing ethylbenzene in an amount of not less than 8% by weight, more preferably not less than 45% by weight. On the other hand, if the ethylbenzene concentration in the feedstock is too high, the amount of xylene contained in the feedstock is relatively small, so that the amount of xylene which can be recovered is decreased and the economic efficiency is reduced. The method is effective when the feedstock used contain ethylbenzene in an amount of not more than 80% by weight.

The feedstock further contains xylene. The xylene content is not restricted, and usually it is about 15% by weight to 91% by weight. Since xylene isomers are generated at a prescribed ratio by subjecting xylene to isomerization step, the ratio among the xylene isomers in the feedstock is not restricted at all. Usually, the percentage of p-xylene based on the xylene isomers contained in the feedstock is about 0 to 24% by weight, the percentage of m-xylene is about 50 to 75% by weight and the percentage of o-xylene is about 25 to 35% by weight. For example, in case of "pyrolysis gasoline", the percentage of p-xylene based on the xylene isomers is about 23% by weight, the percentage of m-xylene is about 53% by weight and the percentage of o-xylene is about 26% by weight. In case of C8 aromatic hydrocarbons from the p-xylene-separating step having a low p-xylene concentration, the percentage of p-xylene based on the xylene isomers is about 0.5% by weight, the percentage of m-xylene is about 73.5% by weight and the percentage of o-xylene is about 26% by weight.

The feedstock may contain an aliphatic hydrocarbon(s) and/or C9 aromatic hydrocarbon(s). Examples of the aliphatic hydrocarbons include n-octane, methylheptane, dimethylhexane, n-nonane, methyloctane, ethylheptane and the like. Examples of the C9 aromatic hydrocarbons include n-propylbenzene, iso-propylbenzene, o-ethylmethylbenzene, m-ethylmethylbenzene, p-ethylmethylbenzene, 1,2,3-trimethylbenzene, 1,2,4-trimethylbenzene, 1,3,5-trimethylbenzene, indane, indene and the like. The total content of these components other than the alicyclic hydrocarbons, ethylbenzene and xylene is not restricted, and usually not more than 30% by weight based on the entire feedstock.

The conversion reaction of ethylbenzene is carried out under a reaction pressure of not lower than 1.0 MPa-G. If the reaction pressure is excessively high, the disproportionation reaction, transalkylation reaction and aromatics ring hydrogenation preferentially occur. Therefore, the reaction pressure is preferably 1.3 MPa-G to 5.0 MPa-G, more preferably 1.7 MPa-G to 3.0 MPa-G. The symbol "-G" means gauge pressure.

The conversion reaction of ethylbenzene is carried out in the presence of hydrogen. Hydrogen is indispensable in order to hydrogenate the ethylene by-produced during the conversion of ethylbenzene to benzene in order to irreversibly proceed the conversion reaction of ethylbenzene. From the viewpoint of inhibiting deactivation of the catalyst, it is desirable to add more hydrogen, on the other hand, from the economical viewpoint, it is desirable to add less hydrogen. The molar ratio of hydrogen to the feedstock (hereinafter referred to as "$H_2/HC$") may be from 3 mol/mol to 15 mol/mol. The $H_2/HC$ range is preferably from 4 mol/mol to 12 mol/mol, more preferably from 5 mol/mol to 10 mol/mol. The best effects are obtained when the $H_2/HC$ is from 5 mol/mol to 9 mol/mol. The hydrogen is supplied to the reaction system in the form of hydrogen gas or a hydrogen-containing gas. Examples of the hydrogen-containing gas include the hydrogen-containing gas obtained by separating at a high pressure the gas obtained in the reforming process of naphtha; the hydrogen-containing gas obtained by separating at a high pressure the gas obtained in thermal cracking of naphtha; the hydrogen-containing gas obtained by separating carbon dioxide from the gas obtained in steam reforming; and the hydrogen-containing gas obtained by highly purifying the above-described hydrogen-containing gas by adsorptive separation.

The reaction temperature in the conversion reaction of ethylbenzene in the present invention is usually from 200° C. to 550° C., preferably from 250° C. to 500° C. The weight hourly spatial velocity (WHSV) which expresses the contact time is from 0.1 $hr^{-1}$ to 50 $hr^{-1}$, preferably from 0.5 $hr^{-1}$ to 20 $hr^{-1}$. In cases where the target ethylbenzene conversion rate is set, by fixing one of the reaction temperature and the weight hourly spatial velocity, the other is determined as a logical consequence. As long as the reaction temperature and "WHSV" are within the ranges described above, they may be arbitrarily selected.

The reaction may be carried out by any of fixed-bed process, moving bed process and fluidized bed process. Among these processes, fixed-bed process is especially preferred because of ease of operation.

The zeolite employed in the catalyst is MFI zeolite. The MFI zeolite can be synthesized by, for example, the method described in Example 1 on pages 4-5 of JP 60-35284 B and Example 1 on page 7 of JP 46-10064 B. Such an MFI per se and the production process thereof are well-known and an example of the synthesis process is also described concretely in Examples below.

The catalytic performance of zeolite varies also depending on the composition, especially on the silica/alumina molar ratio ($SiO_2/Al_2O_3$ molar ratio) and on the size of the crystallite thereof, even when the zeolite structure is the same. The preferred $SiO_2/Al_2O_3$ molar ratio in MFI zeolite is from 20 to 60, more preferably from 25 to 55. The $SiO_2/Al_2O_3$ molar ratio may be attained by controlling the ratio of the components when synthesizing the zeolite. Further, by removing aluminum constituting the zeolite structure with an aqueous acid solution such as hydrochloric acid or with an aluminum-chelating agent such as ethylenediaminetetraacetic acid (EDTA), the silica/alumina molar ratio may be increased. Conversely, by treating the zeolite with aqueous aluminum nitrate solution, aqueous sodium aluminate solution or the like, aluminum may be introduced into the zeolite structure to decrease the silica/alumina molar ratio of the zeolite to attain the preferred silica/alumina molar ratio. The silica/alumina molar ratio may be easily determined by atomic absorption spectrometry, fluorescent X-ray diffraction method, ICP (inductively coupled plasma) spectrometry or the like.

Such a zeolite is appropriately selected and utilized for the formation of the catalyst. Since the synthetic zeolites are generally in the form of powder, it is preferred to mold the zeolite. Examples of the molding methods include compression molding method, roll molding method and extrusion method. Among these molding methods, extrusion method is preferred. In the extrusion method, a binder(s) such as alumina sol, alumina gel, bentonite and/or kaolin, as well as a surfactant(s) such as sodium dodecylbenzene sulfonate, Span (trademark) and/or Tween (trademark), is(are) added as required as a molding aid(s), and kneaded with the powder. As required, a machine such as a kneader is used. The amount of the binder to be added is not restricted, and usually about from 0 to 30 parts by weight, preferably from 10 to 20 parts by weight based on 100 parts by weight of the total of the zeolite and inorganic oxide(s).

To increase the amount of the metal supported on the catalyst used and to promote dispersion, an inorganic oxide(s) such as alumina or titania is added when molding the zeolite. Among the inorganic oxides, alumina is especially preferred. As the alumina, boehmite, boehmite gel, gibbsite, bayerite, nordstrandite, diaspore, amorphous alumina gel and the like are known. Any of these alumina may preferably be used. The amount of the inorganic oxide(s) to be added is not restricted and is usually about from 10 to 700 parts by weight, preferably about from 100 to 400 parts by weight based on 100 parts by weight of the zeolite.

The kneaded product is extruded through a screen. Industrially, an extruder is used. The kneaded product extruded through a screen is in the form of noodle. The size of the molded product is determined by the pore size of the screen. A pore size of the screen of form 0.2 to 2 mm diameter is preferably employed. The molded product in the form of noodle extruded through the screen may preferably be treated with a Marumelyzer (trademark) to round off the edges. The thus prepared molded product is preferably dried at from 50° C. to 250° C. After drying, the molded product is preferably calcined at from 250° C. to 600° C., more preferably at from 350° C. to 600° C.

The thus prepared molded product is then subjected to ion-exchange treatment for giving solid acidity. Examples of the method for giving solid acidity include a method in which the molded product is subjected to ion-exchange treatment with a compound(s) containing ammonium ion (e.g., $NH_4Cl$, $NH_4NO_3$, $(NH_4)_2SO_4$ and the like) to introduce $NH_4$ ions into the ion-exchange sites in the zeolite, and then the $NH_4$ ions are exchanged with hydrogen ions by drying and calcining the zeolite; and a method in which hydrogen ions are directly introduced into the ion-exchange sites of zeolite by treating the zeolite with a compound(s) containing an acid (e.g., HCl, $HNO_3$, $H_3PO_4$ and the like). Since the latter method may break the zeolite structure, the former method is preferred, that is, the zeolite is preferably treated with an ammonium ion-containing compound(s). Alternatively, solid acidity may be added by introducing divalent and/or trivalent metal ions into the ion-exchange sites of zeolite. Examples of the divalent metal ion include $Mg^{2+}$, $Ca^{2+}$, $Sr^{2+}$ and $Ba^{2+}$ which are alkaline earth metals. Examples of the trivalent metal ion include rare earth metal ions such as $Ce^{3+}$, $La^{3+}$ and the like. The method in which the divalent and/or trivalent metal ions are introduced and the method in which ammonium ions are introduced or hydrogen ions are directly introduced may be employed in combination, and this combination may be more preferred in some cases. In the present invention, combinations of ammonium ion and an alkaline earth metal are preferred, and especially preferred one is the combination of ammonium ion and $Ca^{2-}$. The ion-exchange treatment is carried out by a batch process or a continuous flow process in which the catalyst carrier mainly composed of zeolite and the inorganic oxide(s) is treated with a solution containing the ions, usually with an aqueous solution. The concentrations of ammonium ion and $Ca^{2+}$ in the aqueous solution are not restricted, and usually, they are about from 0.5 mol/L to 2.0 mol/L, and about from 0.08 mol/L to 0.40 mol/L, respectively. The treatment temperature is usually between room temperature and 100° C.

After the ion-exchange treatment, rhenium as the hydrogenation-active metal is supported. The role of the hydrogenation-active metal is to quickly hydrogenize the ethyl group generated from the ethylbenzene in the feedstock by dealkylation and the decomposed non-aromatic hydrocarbons in the presence of hydrogen, so as to accelerate the dealkylation and decomposition reactions, thereby inhibiting the generation of oligomers which poison the catalyst. If the amount of the supported hydrogenation-active metal is large, aromatics ring hydrogenation occurs, which is not preferred. On the other hand, if the amount of the supported hydrogenation-active metal is too small, the hydrogenation ability in the deethylation reaction and decomposition reaction of the non-aromatic hydrocarbons is insufficient, so that the catalytic activity is low.

In the conversion reaction of ethylbenzene, a catalyst carrying rhenium as the hydrogenation-active metal is used. The preferred amount of rhenium to be supported is from 0.05% by weight to 2% by weight, more preferably from 0.1% by weight to 1% by weight.

Carrying rhenium is usually conducted by immersing the catalyst in an aqueous solution of a rhenium compound. As the aqueous solution, for example, aqueous perrhenic acid solution, aqueous ammonium perrhenate solution or the like may be employed.

The thus prepared catalyst is preferably dried at from 50° C. to 250° C. for not less than 30 minutes, and is preferably calcined at from 350° C. to 600° C. for not less than 30 minutes before use.

Although the catalyst is, as mentioned above, a catalyst mainly composed of MFI zeolite and an inorganic oxide(s) and supporting rhenium, it may contain a zeolite other than MFI zeolite, and/or a hydrogenation-active metal other than rhenium in an amount not adversely affect the method, that is, in an amount at which the effects of the method are obtained. The term "mainly composed of MFI zeolite and an inorganic oxide(s)" herein means that the total content of the MFI zeolite and the inorganic oxide(s) is more than 50% by weight based on the weight of the catalyst. The total content of the MFI zeolite and the inorganic oxide(s) is preferably not less than 80% by weight, more preferably not less than 90% by weight, still more preferably, the part of the catalyst other than rhenium consists essentially of MFI zeolite and the inorganic oxide(s).

Production processes of p-xylene using the process are now described.

FIG. 1 shows a preferred example of the flow of the production of p-xylene, in which a C8 aromatic hydrocarbon mixture alone containing ethylbenzene and an alicyclic hydrocarbon(s) in a large amount is used. The C8 aromatic hydrocarbon mixture denoted by stream 5 joins C8 aromatic hydrocarbons having a low p-xylene concentration denoted by stream 6 from a p-xylene-separation step 2, and transferred to a xylene-isomerizing step 3 containing a hydrogenation dealkylation catalyst, where they are isomerized to a p-xylene concentration close to that in the thermodynamic equilibrium composition, and simultaneously, the ethylbenzene in the C8 aromatic hydrocarbon mixture and the ethylbenzene in the liquid from the p-xylene-separation step 2 denoted by stream 6 are deethylated to be converted mainly to benzene. To the xylene-isomerizing step 3, hydrogen or a hydrogen-containing gas is also supplied through a line denoted by stream 7. The reaction product is supplied to a low boiling components separation step 4 through a stream 8, and after separating hydrocarbons of C7 or less such as benzene through a line denoted by stream 9, it is supplied to a high boiling components separation step 1 through a stream 10. After separating the aromatic hydrocarbons of mainly C9 or more through a line denoted by stream 12, the reaction product is transferred to the p-xylene-separation step 2 through a stream 11, where the product p-xylene is separated through a stream 13. When using this production process, by employing the process of the present invention in the xylene-isomerizing step, since the feedstock containing an alicyclic hydrocarbon(s), ethylbenzene and xylene is supplied to the p-xylene-separating step after decreasing ethyl benzene in the xylene-isomerizing step while suppressing the increase in the xylene loss, the concentration of p-xylene contained in the C8 aromatic hydrocarbon mixture supplied to the p-xylene-separating step is high and the ethylbenzene concentration is low, so that the load on the p-xylene-separating step can also be decreased, which leads increase in the production of p-xylene.

Figure 2:
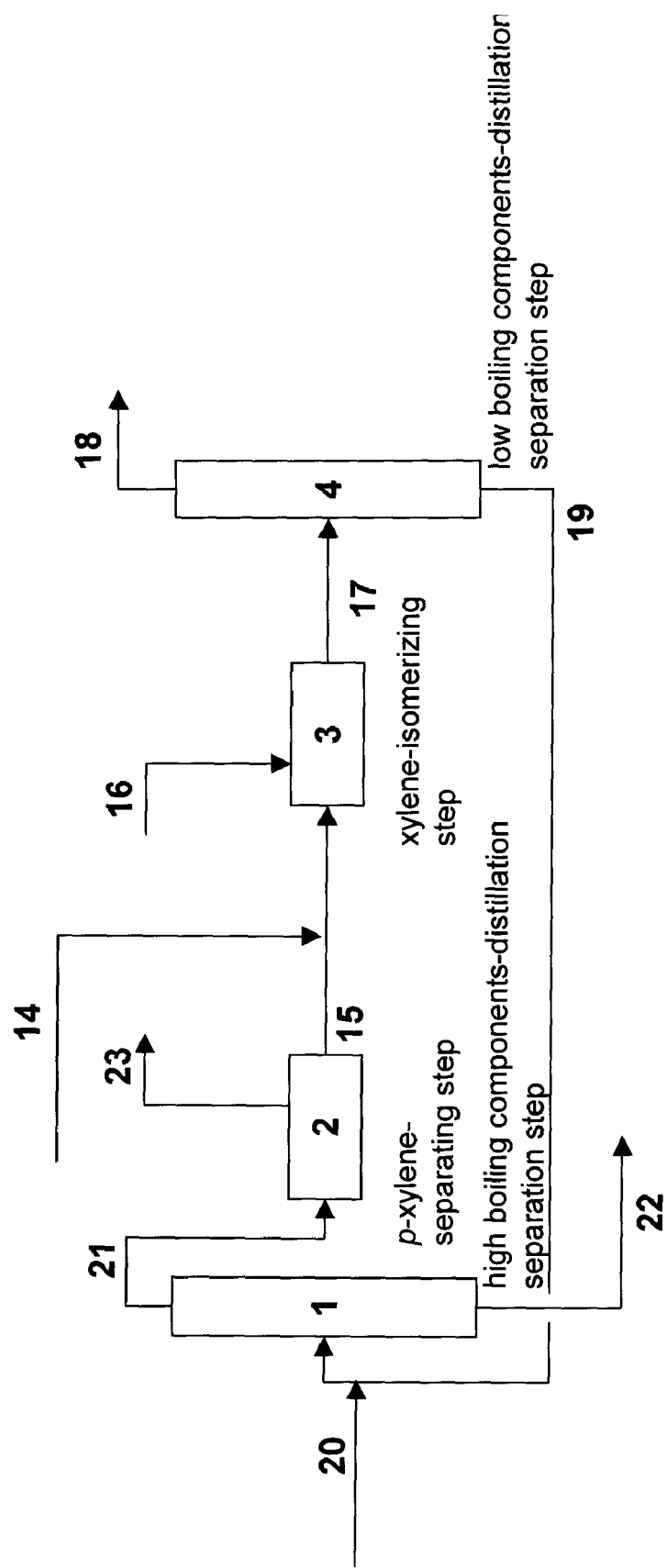
FIG. 2 is a conceptual diagram showing the flow of the "separation-isomerization cycle" for the improved production of p-xylene, to which the process may preferably be applied.

FIG. 2 shows a preferred example of the flow of the production of p-xylene, in which both of a C8 aromatic hydrocarbon mixture containing ethylbenzene and an alicyclic hydrocarbon(s) in a large amount and a C8 aromatic hydrocarbon mixture containing ethylbenzene and an alicyclic hydrocarbon(s) in a small amount are used. The C8 aromatic hydrocarbon mixture containing a large amount of ethylbenzene denoted by stream 14 joins a C8 aromatic hydrocarbons having a low p-xylene concentration denoted by stream 15 from a p-xylene-separation step 2, and transferred to a xylene-isomerizing step 3 containing a hydrogenation dealkylation catalyst, where they are isomerized to a p-xylene concentration close to that in the thermodynamic equilibrium composition, and simultaneously, the ethylbenzene in the C8 aromatic hydrocarbon mixture and the ethylbenzene in the liquid from the p-xylene-separation step 2 denoted by stream 15 are deethylated to be converted mainly to benzene. To the xylene-isomerizing step 3, hydrogen or a hydrogen-containing gas is also supplied through a line denoted by stream 16. The reaction product is supplied to a low boiling components separation step 4 through a stream 17, and after separating hydrocarbons of C7 or less such as benzene through a line denoted by stream 18, it is supplied to a high boiling components separation step 1 through a stream 19. On the other hand, the C8 aromatic hydrocarbon mixture containing ethylbenzene and an alicyclic hydrocarbon(s) in a small amount is supplied to the high boiling components separation step 1 through a stream 20. After separating the aromatic hydrocarbons of mainly C9 or more in the C8 aromatic hydrocarbon mixture denoted by stream 19 and stream 20 through a line denoted by stream 22, the reaction product is transferred to the p-xylene-separation step 2 through a stream 21, where the product p-xylene is separated through a stream 23. When using this production process, by employing the process in the xylene-isomerizing step, since the feedstock containing an alicyclic hydrocarbon(s), ethylbenzene and xylene is supplied to the p-xylene-separating step after decreasing ethylbenzene in the xylene-isomerizing step while suppressing the increase in the xylene loss, the concentration of p-xylene contained in the C8 aromatic hydrocarbon mixture supplied to the p-xylene-separating step is high and the ethylbenzene concentration is low, so that the load on the p-xylene-separating step can also be decreased, which leads increase in the production of p-xylene.

Figure 3:
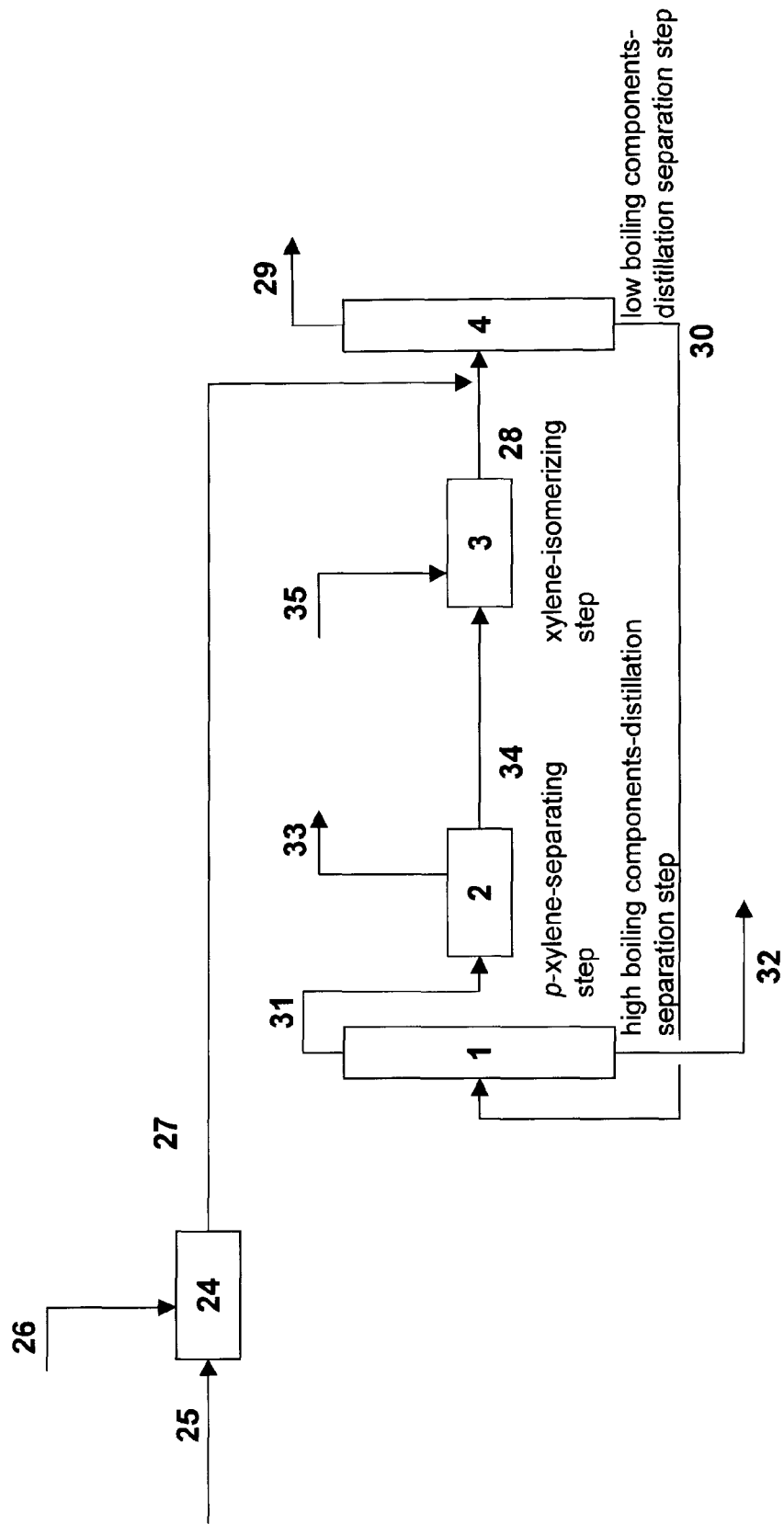
FIG. 3 is a conceptual diagram showing the flow of the "separation-isomerization cycle" for the improved production of p-xylene, to which the process may preferably be applied.
Figure 4:
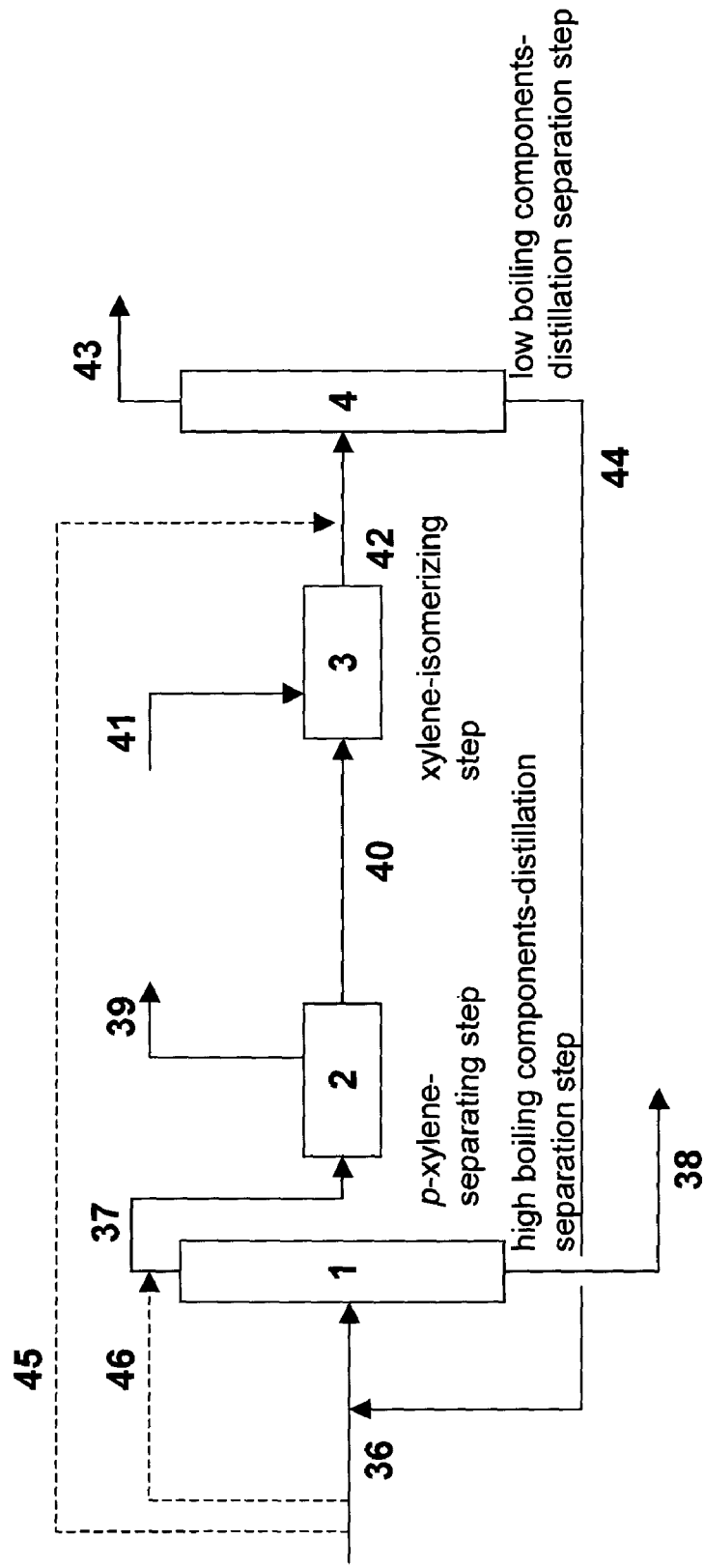
FIG. 4 is a conceptual diagram showing the flow of the "separation-isomerization cycle" for the conventional production of p-xylene.

FIG. 3 shows a preferred example of the flow of the production of p-xylene, in which a C8 aromatic hydrocarbon mixture containing ethylbenzene and an aromatic hydrocarbon(s) in a large amount is supplied to the "separation-isomerization cycle" after converting most of the ethylbenzene contained therein. The C8 aromatic hydrocarbon mixture is supplied to a dealkylation step 24 of ethylbenzene through a supply line denoted by stream 25, where the ethylbenzene contained in the C8 aromatic hydrocarbon mixture is deethylated to be converted mainly to benzene. To the dealkylation step 24 of ethylbenzene, hydrogen or a hydrogen-containing gas is also supplied through a line denoted by stream 26. The obtained reaction product is transferred to a low boiling components separation step 4 through a line denoted by stream 27 together with the C8 aromatic hydrocarbon mixture containing by-products from the xylene-isomerizing step through a line denoted by stream 28. The hydrocarbons of C7 or less such as benzene are separated through a stream 29. The C8 aromatic hydrocarbon mixture from which low boiling components were separated is transferred to a high boiling components separation step 1 through a stream 30, and high boiling components are removed through a line denoted by stream 32. The C8 aromatic hydrocarbon mixture from which the high boiling components were removed is transferred to a p-xylene-separating step 2 through a line denoted by stream 31, and p-xylene is separated and recovered through a line denoted by a stream 33. The C8 aromatic hydrocarbons having a low p-xylene concentration are transferred to a xylene-isomerizing step 3 through a line denoted by stream 34, where they are isomerized to a p-xylene concentration close to that in the thermodynamic equilibrium composition. To the xylene-isomerizing step, hydrogen or a hydrogen-containing gas is also supplied through a line denoted by stream 35. The C8 aromatic hydrocarbon mixture containing by-products, from the xylene-isomerizing step, is transferred to a low boiling components separation step 4 through a line denoted by stream 28, the low boiling components such as benzene and toluene byproduced in the xylene-isomerizing step are separated and removed through a line denoted by a stream 29, and the recycle stream containing high boiling components and having a high p-xylene concentration is transferred to the high boiling components separation step 1 through a line denoted by a stream 30.

The content of the alicyclic hydrocarbons in the feedstock means the content in the feedstock supplied to the xylene-isomerizing step 3 and dealkylation step 24 of ethylbenzene shown in FIGS. 1 to 3 described above.

When using this production process, by employing the process in the dealkylation step of ethylbenzene, the feedstock containing an alicyclic hydrocarbon(s), ethylbenzene and xylene is supplied to the "separation-isomerization cycle" after decreasing ethylbenzene in the dealkylation step of ethylbenzene while suppressing the increase in the xylene loss. By this, since the concentration of the p-xylene contained in the C8 aromatic hydrocarbon mixture to be supplied to the p-xylene-separating step is increased and the ethylbenzene concentration is decreased, the load on the p-xylene-separating step can also be decreased, which leads to the increase in the production of p-xylene. Further, since the ethylbenzene concentration in the "separation-isomerization cycle" is decreased and the xylene loss due to the reaction between ethylbenzene and xylene in the xylene-isomerizing step can be decreased, the raw material unit consumption of p-xylene can be improved.

The method will now be described in more detail by way of examples thereof

EXAMPLES

Synthesis of MFI Zeolite

In 529 g of water, 40.9 g of aqueous sodium hydroxide solution (NaOH content: 48.6% by weight, $H_2O$ content: 51.4% by weight, Mitsuwaka Pure Chemicals Research Institute) and 15.7 g of tartaric acid (tartaric acid content: 99.7% by weight, $H_2O$ content: 0.3% by weight, CaHC CO., LTD.) were dissolved. To this solution, 12.83 g of sodium aluminate solution ($Al_2O_3$ content: 18.9% by weight, NaOH content: 25.4% by weight, $H_2O$ content: 55.7% by weight, Daiso Co., Ltd.) was added and the mixture was made to be a uniform solution. To this solution, 95.2 g of hydrated silisic acid ($SiO_2$ content: 90.4% by weight, NaOH content: 0.22% by weight, $Al_2O_3$ content: 0.26% by weight, $H_2O$ content: 9.12% by weight, Nipseal VN-3, Nihon Silica Co., Ltd.) was slowly added with stirring to prepare an aqueous reaction mixture in the form of uniform slurry. The composition ratio (molar ratio) of this reaction mixture was as follows:

$SiO_2/Al_2O_3$: 55
OH—/$SiO_2$: 0.26
A/$Al_2O_3$: 4.0 (A: tartaric acid salt)
$H_2O/SiO_2$: 22

The reaction mixture was placed in a 1000 ml-autoclave and the autoclave was sealed, followed by allowing the reaction at 160° C. for 72 hours with stirring at 800 rpm. After the reaction, washing of the reaction product with distilled water and subsequent filtration were repeated 5 times, and the resulting product was dried overnight at about 120° C. to obtain MFI zeolite.

Observation of this zeolite with FE-SEM revealed that the average crystallite size was such that the longer axis was 1.8 μm and shorter axis was 1.3 μm.

Fluorescent X-ray diffraction analysis of this zeolite revealed that the $SiO_2/Al_2O_3$ molar ratio thereof was 43.

(Production of Catalyst A)

To the thus synthesized MFI zeolite in an amount of 11 g in terms of the absolute dryness standard (calculated from the loss on ignition after calcining at 500° C. for 20 minutes), hydrated alumina (produced by Sumitomo Chemical Co., Ltd.) having pseudoboehmite structure in an amount of 29 g in terms of the absolute dryness standard, and 60 g of alumina sol ($Al_2O_3$ content: 10% by weight, produced by Nissan Chemical Industries, Ltd.) were added and the mixture was sufficiently mixed, followed by drying the mixture in a dryer at 120° C. until the mixture became a form of clay. The obtained kneaded mixture was extruded through a screen having a pore diameter of 1.6 mm. The extruded molded product was dried overnight at 120° C. Thereafter, the temperature was slowly raised from 350° C. to 500° C., and the product was calcined at 500° C. for 2 hours. Twenty grams of this molded product was placed in an aqueous solution containing 2.2 g of ammonium chloride (Sigma-Aldrich) and 1.3 g of calcium chloride dihydrate (CaHC Co., Ltd.) in 60 g of distilled water, and the resulting mixture was treated at 80° C. for 1 hour with occasional stirring. Thereafter, the aqueous solution was removed, and washing of the reaction product with distilled water and subsequent filtration were repeated 5 times. The resulting product was immersed in 30 mL of an aqueous solution of perrhenic acid containing 120 mg of rhenium in terms of Re at room temperature, and the resulting mixture was left to stand for 2 hours while stirring the mixture every 30 minutes. Thereafter, the product was drained and dried overnight at 120° C., followed by treating the resulting product in a hydrogen sulfide gas flow having a concentration of 17 mmol at 280° C. for 2 hours. Thereafter, the product was calcined in the air at 540° C. for 2 hours. The obtained catalyst is hereinafter referred to as "Catalyst A" for short. The calcium content and sodium content in the catalyst measured by atomic absorption spectrometry were 0.17% by weight in terms of Ca and 0.3% by weight in terms of Na, respectively.

The amount of rhenium supported on the catalyst, measured by ICP spectrometry was 0.5% by weight in terms of Re metal.

(Production of Catalyst B)

Catalyst B was produced in the same manner as in Catalyst A except that the aqueous solution of perrhenic acid contained 80 mg of rhenium in terms of Re (Kisan Kinzoku Chemicals Co., Ltd). The calcium content and sodium content in the catalyst measured by atomic absorption spectrometry were 0.17% by weight in terms of Ca and 0.3% by weight in terms of Na, respectively. The amount of rhenium supported on the catalyst, measured by ICP spectrometry was 0.3% by weight in terms of Re metal.

Example 1

The above-described Catalyst A was charged into the reactor, and a reaction test was carried out. The composition of the feedstock, reaction conditions and the test results are shown in Table 1 below. The analysis of the composition of the feedstock and the reaction products was carried out using 3 gas chromatography equipments with flame ionization detector.

(1) Gas components (components from methane to n-butane in gas):

Column Packings: Unipak S (trademark), 100-150 mesh
Column: made of stainless steel; length: 4 m; inner diameter: 3 mm
$N_2$: 1.65 kg/cm²-G
Temperature: 80° C.

(2) Liquid components with lower boiling points than that of benzene (from methane to n-butane dissolved in the liquid and from 2-methyl-butane to benzene which are liquid components):

Liquid phase: 25% polyethylene glycol 20M
Support: "Shimalite" 60-80 mesh
Column: made of stainless steel; length: 12 m; inner diameter: 3 mm
$N_2$: 2.25 kg/cm²-G
Temperature: from 68° C. to 180° C. at a raising rate of 2° C./min (3) Liquid components with higher boiling points than that of benzene (from benzene to heavy end components)

Spelco wax fused silica capillary: length: 60 m; inner diameter: 0.32 mm; film thickness: 0.5 μm
He linear velocity: 23 cm/sec.
Temperature: from 67° C. to 80° C. at a raising rate of 1° C./min, and from 80° C. to 200° C. at a raising rate of 2° C./min.

TABLE 1

| | Unit | Example 1 | Comparative Example 1 | Comparative Example 2 | Comparative Example 3 | Reference Example 1 | Reference Example 2 | Example 2 | Example 3 | Example 4 |
|---|---|---|---|---|---|---|---|---|---|---|
| Reaction conditions | | | | | | | | | | |
| Temperature | ° C. | 405 | 412 | 405 | 413 | 396 | 387 | 381 | 379 | 376 |
| Pressure | MPa-G | 1.81 | 0.90 | 0.90 | 0.90 | 0.90 | 0.90 | 1.30 | 1.71 | 1.71 |
| H2/HC | mol/mol | 3.0 | 3.0 | 2.9 | 3.0 | 3.0 | 3.0 | 6.0 | 5.8 | 3.1 |
| WHSV | 1/hr | 3.5 | 3.5 | 3.7 | 3.5 | 3.5 | 3.5 | 1.8 | 1.8 | 1.7 |
| Feedstocks | % by weight | | | | | | | | | |
| Cyclohexane | | 15.8 | 15.8 | <0.1 | <0.1 | <0.1 | <0.1 | <0.1 | <0.1 | <0.1 |
| n-octane | | <0.1 | <0.1 | <0.1 | <0.1 | <0.1 | 14.5 | <0.1 | <0.1 | <0.1 |
| Dimethylcyclohexane | | <0.1 | <0.1 | 14.9 | <0.1 | <0.1 | <0.1 | 3.8 | 3.6 | 3.6 |
| Ethylcyclohexane | | <0.1 | <0.1 | <0.1 | 15.0 | <0.1 | <0.1 | <0.1 | <0.1 | <0.1 |
| C8+ Nonaromatic hydrocarbons | | 0.1 | 0.1 | 0.1 | 0.1 | 0.1 | 0.4 | 0.1 | 0.1 | 0.1 |
| Toluene | | 0.1 | 0.1 | 0.1 | 0.1 | 0.1 | 0.1 | 0.1 | 0.1 | 0.1 |
| Ethylbenzene | | 48.9 | 48.9 | 49.4 | 49.3 | 58.1 | 49.5 | 55.6 | 55.8 | 55.8 |

TABLE 1-continued

| | Unit | Example 1 | Comparative Example 1 | Comparative Example 2 | Comparative Example 3 | Reference Example 1 | Reference Example 2 | Example 2 | Example 3 | Example 4 |
|---|---|---|---|---|---|---|---|---|---|---|
| p-xylene | | 7.5 | 7.5 | 7.6 | 7.6 | 9.0 | 7.6 | 8.7 | 8.7 | 8.7 |
| m-xylene | | 18.4 | 18.4 | 18.6 | 18.6 | 21.8 | 18.6 | 21.1 | 21.1 | 21.1 |
| o-xylene | | 9.1 | 9.1 | 9.2 | 9.2 | 10.8 | 9.2 | 10.5 | 10.5 | 10.5 |
| C9+ Aromatic hydrocarbons | | 0.1 | 0.1 | 0.1 | 0.1 | 0.1 | 0.1 | 0.1 | 0.1 | 0.1 |
| Composition of reaction solution | % by weight | | | | | | | | | |
| C5− Nonaromatic hydrocarbons | | 21.4 | 22.5 | 16.7 | 24.3 | 16.0 | 25.6 | 15.4 | 15.2 | 14.5 |
| Cyclohexane | | 2.5 | 3.0 | <0.1 | <0.1 | <0.1 | <0.1 | <0.1 | <0.1 | <0.1 |
| n-octane | | <0.1 | <0.1 | <0.1 | <0.1 | <0.1 | 0.3 | <0.1 | <0.1 | <0.1 |
| Dimethylcyclohexane | | <0.1 | <0.1 | 8.7 | <0.1 | <0.1 | <0.1 | 1.7 | 1.2 | 1.1 |
| Ethylcyclohexane | | <0.1 | <0.1 | <0.1 | 1.2 | <0.1 | <0.1 | <0.1 | <0.1 | <0.1 |
| C8+ Nonaromatic hydrocarbons | | 0.1 | 0.1 | 0.4 | 0.1 | <0.1 | <0.1 | 0.6 | 0.8 | 0.8 |
| Benzene | | 31.0 | 29.6 | 30.6 | 28.5 | 39.5 | 32.9 | 37.3 | 38.1 | 38.4 |
| Toluene | | 7.5 | 7.2 | 9.0 | 9.3 | 2.7 | 3.5 | 4.3 | 3.9 | 4.6 |
| Ethylbenzene | | 3.4 | 3.8 | 2.4 | 3.3 | 2.9 | 4.1 | 3.0 | 2.7 | 2.5 |
| p-xylene | | 7.5 | 7.3 | 7.0 | 7.1 | 9.1 | 7.8 | 8.6 | 8.8 | 8.9 |
| m-xylene | | 17.0 | 16.6 | 16.0 | 16.1 | 20.5 | 17.7 | 19.8 | 20.1 | 19.9 |
| o-xylene | | 7.4 | 7.3 | 7.0 | 7.1 | 8.8 | 7.5 | 8.2 | 8.3 | 8.4 |
| C9+ Aromatic hydrocarbons | | 2.2 | 2.6 | 2.2 | 3.0 | 0.5 | 0.6 | 1.1 | 0.9 | 0.9 |
| BZ selectivity | mol % | 93.5 | 90.2 | 89.3 | 85.2 | 98.4 | 99.6 | 97.3 | 98.5 | 98.7 |
| Degree of conversion to PX | % by weight | 23.5 | 23.4 | 23.3 | 23.4 | 23.7 | 23.6 | 23.5 | 23.7 | 23.9 |
| Degree of conversion of EB | % by weight | 93 | 92 | 95 | 93 | 95 | 92 | 95 | 95 | 95 |
| XY loss | % by weight | 8.1 | 10.1 | 14.7 | 13.7 | 6.5 | 5.5 | 8.1 | 6.7 | 7.0 |
| Degree conversion of C6+ Nonaromatic hydrocarbons | % by weight | 83.5 | 80.6 | 38.8 | 91.3 | — | 97.6 | 41.1 | 47.8 | 49.3 |

Equation 1

$$\text{BZ selectivity} = \frac{(\text{Amount of substance of benzene contained in reaction solution [mol/hr]}) - (\text{Amount of substance of benzene contained in feedstocks [mol/hr]})}{(\text{Amount of substance of ethylbenzene contained in feedstocks [mol/hr]}) - (\text{Amount of substance of ethylbenzene contained in reaction solution [mol/hr]})} \times 100$$

$$\text{Degree of conversion to PX} = \frac{\text{Weight of p-xylene contained in reaction solution [g/hr]}}{\text{Weight of xylene isomers contained in reaction solution [g/hr]}} \times 100$$

$$\text{Degree of conversion of EB} = \frac{(\text{Weight of ethylbenzene contained in feedstocks [g/hr]}) - (\text{Weight of ethylbenzene contained in reaction solution [g/hr]})}{\text{Weight of ethylbenzene contained in feedstocks [g/hr]}} \times 100$$

$$\text{Loss of XY} = \frac{(\text{Weight of xylene isomers contained in feedstocks [g/hr]}) - (\text{Weight of xylene isomers contained in reaction solution [g/hr]})}{\text{Weight of xylene isomers contained in feedstocks [g/hr]}} \times 100$$

BZ: benzene, PX: p-xylene, EB: ethylbenzene, XY: xylene

Examples 2 to 4, Comparative Examples 1 to 3, Reference Examples 1 and 2

Reactions were conducted in the same manner as in Example 1 except that the compositions of the feedstock and the reaction conditions were as shown in Table 1. The test results are shown in Table 1 described above.

Example 1 and Comparative Example 1 show the results of the reactions wherein a feedstock containing 15.8% by weight of cyclohexane which is an alicyclic hydrocarbon was subjected to the reaction under the same conditions except that the reaction pressure was 1.8 MPa-G and 0.9 MPa-G, respectively, and the reaction temperature was adjusted so as to attain substantially the same ethylbenzene conversion rate. It can be seen from the results that by increasing the reaction pressure from 0.9 MPa-G to 1.8 MPa-G, the xylene loss was reduced by about 20 weight %, benzene selectivity was improved by 3.3 mol %, and the conversion rate to p-xylene was improved by 0.1% by weight.

In Comparative Examples 2 and 3, the reactions were carried out under the same conditions as in Comparative Example 1 except that the alicyclic hydrocarbons added to the feedstock were dimethylcyclohexane and ethylcyclohexane, respectively. Although the influence varies depending on the type of the added alicyclic hydrocarbon, in either case, when the reaction pressure was 0.9 MPa-G, the xylene loss and the benzene selectivity were largely impaired. It can also be seen that in cases where the feedstock contains dimethylcyclohexane or ethylcyclohexane which are alkylcycloalkanes, increase in the xylene loss is prominent.

Reference Examples 1 and 2 show the results of the reactions wherein a feedstock to which neither an alicyclic hydrocarbon nor aliphatic hydrocarbon was added was reacted, and the result wherein a feedstock to which n-octane which is an aliphatic hydrocarbon was added in an amount of 15% by weight in place of the alicyclic hydrocarbon was reacted, respectively. With the feedstock to which only the alicyclic hydrocarbon was added, the xylene loss and the benzene selectivity were substantially the same as those obtained when a feedstock to which neither an alicyclic hydrocarbon nor aliphatic hydrocarbon was added. Thus, it can be seen that increase in the xylene loss and decrease in the benzene selectivity are phenomena specific to the cases where the feedstock contains an alicyclic hydrocarbon, and that even if an aliphatic hydrocarbon is added, increase in the xylene loss or decrease in the benzene selectivity does not occur.

Examples 2 and 3 show the results of the reactions wherein a feedstock containing about 4% by weight of dimethylcyclohexane which is an alicyclic hydrocarbon was subjected to the reaction under the same conditions except that the reaction pressure was 1.3 MPa-G and 1.7 MPa-G, respectively, and the reaction temperature was adjusted so as to attain substantially the same ethylbenzene conversion rate. From the comparison of these results, it can be seen that the higher the reaction pressure, the better the xylene loss, benzene selectivity and conversion rate to p-xylene.

Example 4 shows the results of the reaction carried out under the same conditions as in Example 2 except that $H_2$/HC was 3.1 mol/mol, and the reaction temperature was adjusted so as to attain substantially the same ethylbenzene conversion rate. From the comparison between Examples 2 and 4, it can be seen that by keeping the reaction pressure at not less than 1.0 MPa-G, the influences by the decrease in $H_2$/HC on the xylene loss and benzene selectivity were small.

Example 5

Figure 5:
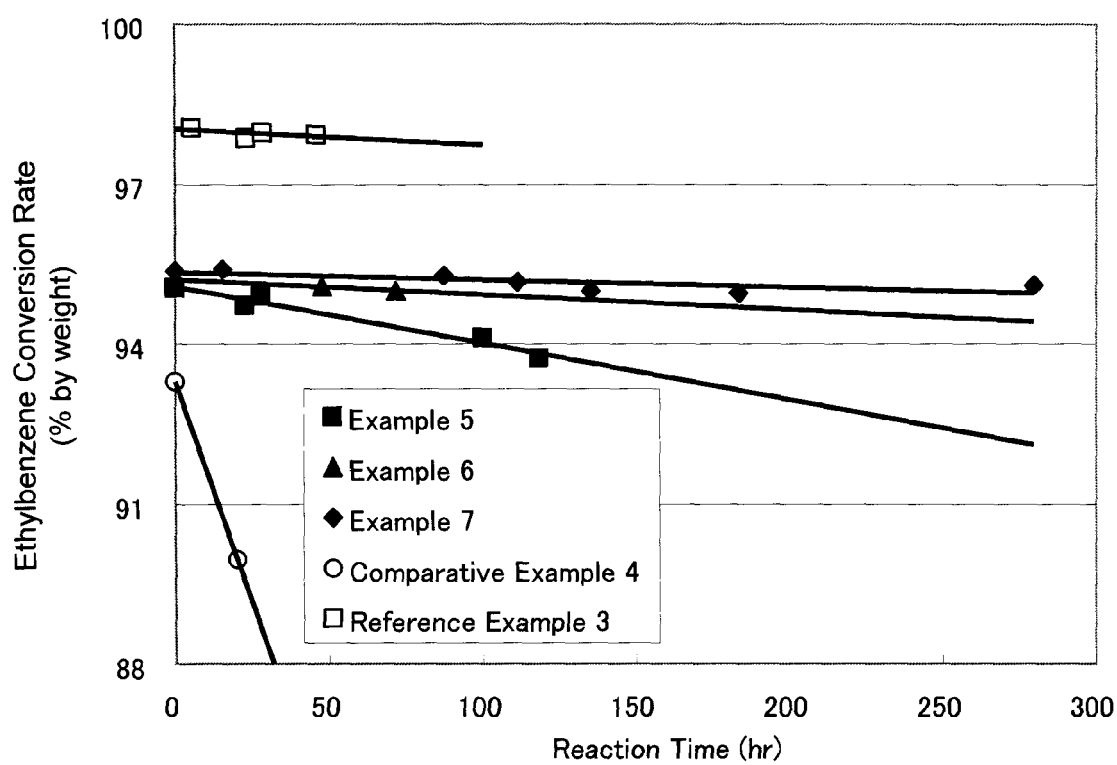
FIG. 5 shows the results of Examples 5 to 7, Comparative Example 4 and Reference Example 3.

The reaction was continued keeping the conditions employed in Example 4 and the relationship between the reaction time and the ethylbenzene conversion rate was examined. The results are shown in FIG. 5. The deactivation rate based on ethylbenzene conversion rate was 0.25% by weight per day.

Example 6

The reaction was continued keeping the conditions employed in Example 2 and the relationship between the reaction time and the ethylbenzene conversion rate was examined. The results are shown in FIG. 5. The deactivation rate based on ethylbenzene conversion rate was 0.03% by weight per day.

Example 7

The reaction was continued keeping the conditions employed in Example 3 and the relationship between the reaction time and the ethylbenzene conversion rate was examined. The results are shown in FIG. 5. The deactivation rate based on ethylbenzene conversion rate was 0.07% by weight per day.

Comparative Example 4

The reaction was continued keeping the conditions employed in Comparative Example 3 and the relationship between the reaction time and the ethylbenzene conversion rate was examined. The results are shown in FIG. 5. The deactivation rate based on ethylbenzene conversion rate was 4.0% by weight per day.

Reference Example 3

The reaction was continued keeping the same conditions as in Reference Example 1 except that the reaction temperature was 403° C., and the relationship between the reaction time and the ethylbenzene conversion rate was examined. The results are shown in FIG. 5. The deactivation rate based on ethylbenzene conversion rate was 0.01% by weight per day.

Example 5 shows the result of the reaction wherein the reaction pressure was 1.3 MPa-G, Examples 6 and 7 show the results of the reaction wherein the reaction pressure was 1.7 MPa-G, and Comparative Example 4 shows the result of the reaction wherein the reaction pressure was 0.9 MPa-G. Reference Example 3 shows the result of the reaction wherein a feedstock not containing an alicyclic hydrocarbon was subjected to the reaction and the reaction pressure was 0.9 MPa-G. From the comparison between Examples 5 and 6 and Comparative Example 4, it can be seen that when the reaction pressure was not less than 1.0 MPa-G, the deactivation rate of the ethylbenzene conversion rate can be decreased. From the comparison between Examples 6 and 7 and Reference Example 3, it can be seen that when the reaction pressure was not less than 1.0 MPa-G and the $H_2$/HC was high, the deactivation rate can be further largely reduced to the level wherein an alicyclic hydrocarbon is not contained.

Example 8, Comparative Example 5, Reference Examples 4 and 5

Reactions were carried out in the same manner as in Example 1 except that the compositions of the feedstock and the reaction conditions were changed as shown in Table 2, and that Catalyst B was used. The test results are shown in Table 2.

TABLE 2

| | Unit | Example 8 | Comparative Example 5 | Reference Example 4 | Reference Example 5 |
|---|---|---|---|---|---|
| Reaction conditions | | | | | |
| Temperature | ° C. | 369 | 370 | 369 | 370 |
| Pressure | MPa-G | 1.00 | 0.65 | 1.00 | 0.65 |
| H2/HC | mol/mol | 3.1 | 3.1 | 3.1 | 3.1 |
| WHSV | 1/hr | 5.0 | 5.0 | 5.1 | 5.0 |
| Feedstocks | % by weight | | | | |
| Cyclohexane | | <0.1 | <0.1 | <0.1 | <0.1 |
| n-octane | | <0.1 | <0.1 | <0.1 | <0.1 |

TABLE 2-continued

|  | Unit | Example 8 | Comparative Example 5 | Reference Example 4 | Reference Example 5 |
|---|---|---|---|---|---|
| Dimethylcyclohexane |  | <0.1 | <0.1 | <0.1 | <0.1 |
| Ethylcyclohexane |  | 1.0 | 1.0 | <0.1 | <0.1 |
| C8+Nonaromatic hydrocarbons |  | <0.1 | <0.1 | <0.1 | <0.1 |
| Toluene |  | 0.3 | 0.3 | 0.3 | 0.3 |
| Ethylbenzene |  | 8.3 | 8.3 | 8.4 | 8.4 |
| p-xylene |  | 0.7 | 0.7 | 0.7 | 0.7 |
| m-xylene |  | 66.0 | 66.0 | 66.8 | 66.8 |
| o-xylene |  | 23.4 | 23.4 | 23.7 | 23.7 |
| C9+Aromatic hydrocarbons |  | 0.2 | 0.2 | 0.2 | 0.2 |
| Composition of reaction solution | % by weight |  |  |  |  |
| C5-Nonaromatic hydrocarbons |  | 2.0 | 2.0 | 1.8 | 1.7 |
| Cyclohexane |  | <0.1 | <0.1 | <0.1 | <0.1 |
| n-octane |  | <0.1 | <0.1 | <0.1 | <0.1 |
| Dimethylcyclohexane |  | <0.1 | <0.1 | <0.1 | <0.1 |
| Ethylcyclohexane |  | 0.6 | 0.6 | <0.1 | <0.1 |
| C8+Nonaromatic hydrocarbons |  | <0.1 | <0.1 | <0.1 | <0.1 |
| Benzene |  | 3.7 | 3.5 | 3.8 | 3.9 |
| Toluene |  | 1.6 | 1.7 | 1.1 | 1.1 |
| Ethylbenzene |  | 3.0 | 3.0 | 3.0 | 2.9 |
| p-xylene |  | 20.6 | 20.5 | 21.0 | 20.9 |
| m-xylene |  | 47.4 | 47.5 | 48.1 | 48.2 |
| o-xylene |  | 20.5 | 20.5 | 20.7 | 20.8 |
| C9+Aromatic hydrocarbons |  | 0.6 | 0.7 | 0.5 | 0.5 |
| BZ selectivity | mol % | 95.1 | 89.6 | 96.7 | 97.3 |
| Degree of conversion to PX | % by weight | 23.3 | 23.1 | 23.4 | 23.3 |
| Degree of conversion of EB | % by weight | 63 | 63 | 64 | 65 |
| Loss of XY | % by weight | 1.8 | 2.0 | 1.6 | 1.4 |
| Degree conversion of C6+Nonaromatic hydrocarbons | % by weight | 41.2 | 39.3 | — | — |

Reference Examples 4 and 5 show the results of the reactions wherein a feedstock not containing an alicyclic hydrocarbons was reacted under the reaction pressures of 1.0 MPa-G and 0.65 MPa-G, respectively, at the same temperature. From the comparison of these results, it can be seen that with a feedstock to which an alicyclic hydrocarbon was not added, by decreasing the reaction pressure, the xylene loss is decreased and the benzene selectivity is increased. Example 8 and Comparative Example 5 show the results of the reactions wherein a feedstock to which ethylcyclohexane which is an aliphatic hydrocarbon was added in an amount of 1.0% by weight was reacted under reaction pressures of 1.0 MPa-G and 0.65 MPa-G, respectively, at the same temperature. With the feedstock containing an alicyclic hydrocarbon, surprisingly, conversely to the cases where an alicyclic hydrocarbon is not added to the feedstock, by increasing the reaction pressure, the benzene selectivity can be promoted and the xylene loss can be decreased.

INDUSTRIAL APPLICABILITY

Since we provide a process for producing p-xylene from a C8 aromatic hydrocarbon mixture, by which xylene loss is small, the deactivation rate of the catalyst can be reduced, and a high conversion rate to p-xylene can be attained, as well as a process for converting ethylbenzene therefor, the method is useful in the field of the production of p-xylene.

The invention claimed is:

1. A process for converting ethylbenzene comprising:
contacting a feedstock containing an alicyclic hydrocarbon(s) in an amount of not less than 1.0% by weight, ethylbenzene and xylene with hydrogen in the presence of a catalyst at a reaction pressure of not less than 1.0 MPa-G to convert ethylbenzene mainly to benzene, wherein said catalyst is mainly composed of MFI zeolite and an inorganic oxide(s) and supports rhenium.

2. The process according to claim 1, wherein the ratio of said hydrogen to said feedstock is not less than 3 moles per 1 mole of said feedstock.

3. The process according to claim 2, wherein said ratio of said hydrogen to said feedstock is not less than 15 moles per 1 mole of said feedstock.

4. The process according to claim 1, wherein content of said alicyclic hydrocarbon(s) in said feedstock is not less than 3.0% by weight.

5. The process according to claim 1, wherein content of said alicyclic hydrocarbon(s) in said feedstock is not more than 16% by weight.

6. The process according to claim 1, wherein said reaction pressure is 1.3 MPa-G to 5.0 MPa-G.

7. The process according to claim 6, wherein said reaction pressure is 1.7 MPa-G to 3.0 MPa-G.

8. The process according to claim 1, wherein said alicyclic hydrocarbon(s) is(are) cycloalkane(s).

9. The process according to claim 8, wherein said cycloalkane(s) is(are) an alkylcycloalkane(s).

10. The process according to claim 1, wherein the content of said supported rhenium is 0.05% by weight to 2% by weight based on the entire catalyst.

11. The process according to claim 1, wherein said inorganic oxide(s) is(are) alumina and/or titania.

12. A process for producing p-xylene, said process comprising:

subjecting a feedstock containing an alicyclic hydrocarbon(s) in an amount of not less than 1.0% by weight, ethylbenzene and xylene to said process according to claim 1, thereby converting said ethylbenzene in said feedstock to mainly benzene;

purifying C8 aromatics hydrocarbon mixture from the obtained reaction product by distillation; and feeding purified C8 aromatics hydrocarbon mixture to a p-xylene separation step.

* * * * *

UNITED STATES PATENT AND TRADEMARK OFFICE
CERTIFICATE OF CORRECTION

| | | |
|---|---|---|
| PATENT NO. | : 8,071,832 B2 | Page 1 of 1 |
| APPLICATION NO. | : 12/933118 | |
| DATED | : December 6, 2011 | |
| INVENTOR(S) | : Yoshikawa et al. | |

It is certified that error appears in the above-identified patent and that said Letters Patent is hereby corrected as shown below:

In Column 13

At line 43, please change "$Ca^{2-}$" to -- $Ca^{2+}$ --.

Signed and Sealed this
Twenty-ninth Day of May, 2012

David J. Kappos
*Director of the United States Patent and Trademark Office*